(12) United States Patent
Bert et al.

(10) Patent No.: US 8,471,228 B2
(45) Date of Patent: Jun. 25, 2013

(54) FAST SCANNING OF A TARGET REGION

(75) Inventors: Christoph Bert, Aschaffenburg (DE);
Thomas Haberer, Frankfurt (DE); Eike Rietzel, Weiterstadt (DE)

(73) Assignees: GSI Helmholtzzentrum fur Schwerionenforschung GmbH (DE); Siemens AG (DE); Forschungszentrum Dresden-Rossendorf E.V. (DE); Heidelberger Ionenstrahltherapie (HIT) Betriebs-Gesellschaft AM Universitatsklinikum Heidelberg mbH (DE)

(*) Notice: Subject to any disclaimer, the term of this patent is extended or adjusted under 35 U.S.C. 154(b) by 157 days.

(21) Appl. No.: 13/120,948

(22) PCT Filed: Sep. 12, 2009

(86) PCT No.: PCT/EP2009/006626
§ 371 (c)(1),
(2), (4) Date: Aug. 26, 2011

(87) PCT Pub. No.: WO2010/034419
PCT Pub. Date: Apr. 1, 2010

(65) Prior Publication Data
US 2011/0303857 A1 Dec. 15, 2011

(30) Foreign Application Priority Data
Sep. 26, 2008 (DE) .................... 10 2008 048 916

(51) Int. Cl.
*A61N 5/10* (2006.01)
*A61N 5/00* (2006.01)
*G21K 5/00* (2006.01)

(52) U.S. Cl.
USPC ............... 250/505.1; 250/492.1; 250/492.3; 250/398; 250/393; 600/1; 315/500

(58) Field of Classification Search
USPC ..... 250/505.1, 492.1, 492.3, 398, 393; 600/1; 315/500
See application file for complete search history.

(56) References Cited

U.S. PATENT DOCUMENTS

| 2005/0238134 A1 | 10/2005 | Brusasco et al. |
| 2011/0306818 A1* | 12/2011 | Bert et al. ................... 600/1 |

(Continued)

FOREIGN PATENT DOCUMENTS

| DE | 199 071 38 A1 | 8/2000 |
| DE | 19907097 A1 | 8/2000 |

(Continued)

OTHER PUBLICATIONS

Bert, Christoph"Bestrahlungsplanung fur bewegte Zielvolumina in der Tumortherapie mit gescanntem Kohlenstoffstrahl" Feb. 3, 2006 XP002481370 Internet Citation.

(Continued)

*Primary Examiner* — Nikita Wells
(74) *Attorney, Agent, or Firm* — Reising Ethington PC

(57) ABSTRACT

The invention concerns a method for irradiating a target with a beam approaching target points, involving the following steps: Measuring at least one of the parameters relating to the position of the beam and the intensity of the beam, changing the beam as a function of the at least one measured parameter, particularly as a function of a variance relating to the at least one measured parameter. The method is characterized in that the at least one measured parameter is measured at the most once per target point. Furthermore, the invention concerns a device for irradiating a target in accordance with the invention-based method and a control system for controlling such a device.

12 Claims, 3 Drawing Sheets

U.S. PATENT DOCUMENTS

2012/0187314 A1* 7/2012 Bert et al. .................. 250/492.3
2012/0241635 A1* 9/2012 Luechtenborg et al. ...... 250/389
2012/0273666 A1* 11/2012 Bert et al. .................. 250/252.1

FOREIGN PATENT DOCUMENTS

| DE | 100 57 824 A1 | 6/2002 |
| EP | 0986070 A1 | 3/2000 |
| EP | 1041579 A1 | 10/2000 |
| EP | 1045399 A1 | 10/2000 |
| EP | 1905481 A2 | 4/2008 |
| JP | 2005329252 A | 12/2002 |
| WO | WO0241948 A1 | 5/2002 |

OTHER PUBLICATIONS

Haberer, Thomas "Magnetic Scanning System for Heavy ion Therapy" Nuclear Instruments and Methods in Physics Research, section—Accelerators Jun. 10, 1993 XP000385496.

Anonymous "Steuerungstechnik" Wikipedia, der freien Enzyklopadie Online XP002560594 Dec. 15, 2009.

* cited by examiner

| Measuring the position of the beam – at most once per screen dot and/or |
| Measuring the intensity of the beam – at most once per screen dot |

| Changing the beam depending on an error concerning position and/or intensity |

Measures concerning the determination of the position or the intensity of the beam:

- intensity control; at the most one position measurement per screen dot

- at the most one position measurement for three or 10 screen dots or even for one line of screen dots;

- at the most one intensity measurement for three or 10 screen dots or even for one line of screen dots;

- performing intensity measurements and/or position measurements according to fixed intervals;

- intensity control of the irradiation process; fixed intervals for the position measurements;

- averaging a measurement over several screen dots;

- taking into consideration the ionization in the detector gas for improving such an averaging process;

- timing of irradiation

- taking into consideration the extraction profile in such timing;

- measuring the beam position spaced from the target;

- the measurement of the width of the beam is performed with a separate module

- connecting measuring devices in series

FIG 3

Measures concerning a change of the beam based on a determination of the position and/or the intensity of the beam:

- Interrupting the irradiation process

- Correcting the beam position

FAST SCANNING OF A TARGET REGION

The present invention concerns a method and a device for irradiating a target with a beam approaching target points and a control system for controlling the invention-based device.

The irradiation of a target with a beam approaching different target points (beam scanning) is already known. For example, when irradiating tumors, particle beams, especially ion beams, in particular with protons, αparticles or carbon nuclei, are used. The beam approaches parts of the target area, the target points, in sequence, one after the other.

Particle beams are especially advantageous for irradiating a target volume because towards their end they pass through a maximum in energy deposition (Bragg-Peak). In this way, it is possible to irradiate effectively even imbedded three-dimensional structures without causing a lot of damage to the imbedding surroundings. Often, three-dimensional target regions are irradiated in layers wherein the radiation energy determining the depth of penetration is selected to be constant (iso-energy layer). A generally known method is also the so-called volumetric scanning in which the successively approached target points are not necessarily assigned to individual (iso-energy) layers. Basically, the invention concerns also embodiments in which the beam is formed by electro-magnetic waves. Furthermore, the invention concerns also embodiments for irradiating plane target regions.

Scanning methods allow for irradiation that is adapted to the shape of the target by scanning with a beam. Distinctions are made between different scanning methods.

In the so-called spot-scan method and the pixel-scan method, the particle beam lingers at each target point for a pre-determined time period and/or deposits at each target point a predetermined number of particles and is turned off when deflecting magnets (scanning magnets) are adjusted to a next target point.

In so-called grid scanning, the particle beam lingers at each of several screen dots during a predetermined time period or deposits at each screen dot a predetermined number of particles. However, between the screen dots, the particle is not or not always turned off. The screen dots can differ from the target points, because the screen dots are usually indicated in the coordination system of the irradiation device, while the target points are usually observed in the coordination system of the target. In particular, the screen dots and the target points do not have to be mutually congruent, although this is preferred. To simplify matters, the points approached during grid scanning are subsequently not always described as screen dots, but also as target points.

In so-called continuous scanning methods, the target points form connected lines, i.e., they form continuous (or quasi-continuous) amounts, wherein their number can be approximately countably infinite. In a continuous scanning method, the particle beam is continuously deflected, at least within a line or row in an iso-energy layer, and scans the target points without lingering at individual places. By means of a depth modulation device, it is also possible to carry out a continuous scanning method in which the depth of penetration is continuously modulated.

Furthermore, so-called uniform scanning is known wherein a homogeneous dose deposition is achieved in a respective iso-energy layer in that once or even several times an equal particle number is deposited at all target points or along the scan paths.

The succession of the target points, the path, can basically run within an iso-energy layer by deflecting the beam merely in its traveling direction, i.e., one- or two-dimensionally lateral. However, the beam can also run between iso-energy layers by changing the energy of the beam.

It is basically known to measure the position of the beam or its three-dimensional position during the irradiation process. It is also known to measure the intensity of the beam, for example, as particle flux or applied particle number, during the irradiation process. To simplify matters, the term intensity is here used in a uniform manner for all respective parameters.

The publication "Magnetic scanning system for heavy ion therapy", Haberer et al, Nuclear Instruments and Methods in Physics Research A330 (1993) 296 ff. shows, for example, a multi-wire-proportional-chamber (MWPC) in order to measure the position of the beam during the irradiation process. Furthermore, the publication shows to measure the intensity of the beam and to use the results of the measurement for controlling irradiation (intensity control). For example, the beam is moved faster when the dose to be deposited per target point is relatively small and the beam intensity is high. The beam is moved correspondingly slower when the dose to be deposited per target point is relatively high and the beam intensity is low. In other words: The beam is directed to the respective next target point when the required particle number has been deposited at the preceding target point.

Basically, it is also known among experts to use the measured position of the beam and its measured intensity for the purpose of making corrections during the irradiation process if differences from the reference values occur. If required, irradiation is even interrupted, for example, in the case of a greater variance from the reference value. So far, such interruptions are made several times per target point in order to achieve a high level of accuracy of measurements. This applies to the position of the beam, as well as to its intensity. In addition, it is possible to measure the beam width.

To have sufficient time for the position measurements, it is known to adjust the beam intensity in such a way that the measurements can be made for each target point. Often, the beam intensity selected for this purpose is lower than can be provided by the accelerator.

The present invention is based on the objective of providing an advantageous method and an advantageous device to irradiate a target with a beam approaching target points, as well as a control system to control the invention-based device.

The objective is achieved by a method for irradiating a target with a beam approaching target points which involves the following steps: Measuring at least one of the parameters relating to the position of the beam and the intensity of the beam, changing the beam as a function of the at least one measured parameter, particularly as a function of a variance relating to the at least one measured parameter. The method is characterized in that the at least one measured parameter is measured at the most once per target point.

The dependent claims specify preferred embodiments of the invention which are subsequently described in more detail.

The invention is based on the observation that the measurement of the position of the beam and the measurement of the intensity of the beam require minimal time. Furthermore, it is based on the knowledge that the measuring cycles described above limit the scanning velocity.

Especially when the beam intensity is adjusted in such a way that it is possible to perform several position measurements per target point, irradiation time as a whole can be quite long, in particular, if the target is approached with several scans (Rescanning, see below). Moreover, the relatively low intensity has a negative effect on the signal-to-noise ratio of the intensity measurement.

It has also been determined that the accuracy regarding the beam position and/or the beam intensity or the knowledge of the beam width achieved through repeated measurements is not particularly necessary, for example, because the device is designed for a respective precise beam guidance, or because it is particularly error tolerant due to a special irradiation arrangement (Rescanning, see below).

It is the idea of the invention to measure the parameters to be measured, i.e., the position of the beam and/or the intensity of the beam, at the most once per target point. The invention includes the case wherein merely one of the two parameters is measured at the most once per target point. In particular, it includes the cases wherein one of the two parameters is measured several times per target point, or not at all, or distributed over several target points, and the respective other parameter is measured merely once per target point.

Current technology allows for intensity measurements that are considerably faster than position measurements. Correspondingly, in a referred embodiment, the position measurement is performed once per target point, while intensity measuring is performed several times per target point.

It is especially preferred to determine the scanning velocity based on the measured intensity of the beam (Intensity control, see above) and, if necessary, to measure the intensity of the beam several times per target point, while the position of the beam is determined at the most once per target point.

The position and/or intensity measurements can be used to determine a variance from predetermined values or reference values; in other words, to determine errors. Changes of the beam can be associated with such determinations. In the easiest case, irradiation is interrupted or even discontinued when the results of the position measurement and/or the results of the intensity measurement exceed a specific variance. In the context of the invention, it is also possible to correct the position and/or the intensity of the beam depending on the amount of the variance.

It is especially preferred to use the measurement of one of the two parameters or even both parameters merely for monitoring the beam, and to interrupt irradiation in case a variance is exceeded. In a preferred embodiment, the measurements are not used for correcting the beam. For example, this can save time spent for correcting the adjustment of the scanning magnets (see example) during the process of irradiation.

Besides irradiating people or animals, it is relevant to irradiate organic materials, particularly cells, or even to irradiate inorganic materials, such as plastic materials, for example, in the context of material research.

It is preferable to use the method of grid scanning, it allows for a particularly fast scanning process.

In the generally known method of multiple irradiation with a beam approaching different target points (rescanning), an intended dose is applied successively during one session with several scans which are separated by short breaks, if required. In the process, within the individual scans, several target points, not necessarily all of them, are irradiated in sequence. In the course of the session, usually a good portion of the target points, or all target points, and thus a good portion of the target area, or the target area as a whole are irradiated several times. The cumulative dose per target point to be applied during the session is distributed to the individual scans, for example, equally or, if required, with different amounts. Even the method of multiple irradiation can be performed in layers or volumetrically.

Especially for rescanning, it is advantageous to use a high scanning velocity because the path to be covered per session when using several scans is clearly longer in comparison to depositing the entire dose in a single scan. Without the invention, the irradiation time as a whole can be too long, for example, because the irradiation process is too encumbering for a person to be irradiated. Immobilization becomes worse with time. The performance of the equipment is relatively low.

Rescanning allows for the use of the invention even in equipments that work less accurate because inaccuracies in the beam position and in beam intensity are kept at a minimum by averaging the performance over several scans. When the method of multiple irradiation is coordinated respectively, it is not necessary to know the precise beam position or beam intensity during the process of irradiation.

If intensity measurements can be performed faster than position measurements, it is recommended even in the context of rescanning to control the beam by means of its intensity and to perform position measurements at the most once per target point.

If a moved target is irradiated, it is advantageous to use rescanning. This is the case because the movement of the target results in variances from the intended dose distribution. This can happen also as a result of interferences between the irradiation procedure and the movement of the target. If irradiation is performed with several scans, such dose errors can be averaged. In the context of particle therapy, such a moved target can involve a tumor in the vicinity of the lung of a person to be irradiated which is moved cyclically up and down because of breathing.

Preferably, the at least one measured parameter is measured at the most once for at least two target points; even more preferably in the sequence mentioned at the most once for three target points, 10 target points or one line of target points. It is especially preferred to keep the number of measurements so low that the time required for the measurements no longer limits the scanning speed. For example, this can be the case with intensity-controlled irradiation when the time required for applying the predetermined dose in several target points exceeds the time for the position measurements of these target points.

If a measurement for several target points is performed at the most once, and if the measurement requires more time than the irradiation of the individual target points, it results in an average value averaged over several target points. For example, in intensity-controlled irradiation, the beam intensity usually varies from target point to target point, resulting in an inhomogeneous distribution.

In order to obtain a most meaningful average value, especially with respect to position measurements and, if necessary, measurements of the beam width, it can be advantageous to take into consideration also timing effects, such as detector performances, for example, the distribution of ionization in the detection gas. This can be especially helpful for a precise correction of the beam position during the irradiation process.

In a preferred embodiment of the invention, the points in time of measurements for the at least one measured parameter are determined by the time that elapsed during the irradiation process.

For example, each measurement of a respective parameter can be performed after the cycle of a fixed interval, ideally in the fastest possible succession, i.e., the shortest possible interval. With this method, the intervals of the measurements are respectively independent from approaching the target points. In other words: approaching the target points and the measurements of the beam position and/or beam intensity are performed in asynchronous manner. For example, it is possible to select different intervals for the position measurements and the intensity measurements. In such a case, the position measurements and the intensity measurements are also asynchronous in relation to each other.

It can also be advantageous to control the irradiation by means of the intensity of the beam and to measure the position of the beam repeatedly each after a respective fixed time interval. Even in this case, the measurements of both parameters are asynchronous with respect to each other, and the measurement of the position of the beam is asynchronous with regard to approaching the target points.

In order to apply a specific dose in a specific target point by means of time control, that is, when approaching the target points is determined by means of the elapsed time, a scanning velocity is selected for the beam that allows for expecting that the intended dose is applied at this point. When the beam lingers at a target point, it is directed to the next target point as soon as a specific time has elapsed which allows for expecting that the intended dose has been applied.

However, such time control does not exclude that knowledge about the properties of a beam can be included. It is therefore preferred to take into consideration the extraction profile of the beam source. In fact, it is possible that in time the number of extracted particles greatly varies, depending on the source. Usually, the extraction profile for a specific source is known. For example, it can be determined prior to irradiation. In the simple case of a homogenous intended dose distribution, this means that a comparatively fast scanning speed is selected when according to the extraction profile the particle number is high. When according to the extraction profile the particle number is low, a comparatively slow scanning velocity is selected. If the intended dose distribution is not homogenous, this has to be also taken into consideration by means of weighting. If a medium beam intensity and a respective scanning velocity is assumed without taking the extraction profile into consideration, the scanning velocity has to be increased comparatively when according to the extraction profile the beam intensity is high, and the scanning velocity has to be reduced when according to the extraction profile the beam intensity is low. In this way, it is possible to reduce variances from the intended dose distribution. The particle amount to be applied can be maintained in a more precise manner.

Some detector types, for example, multi-wire proportional chambers, can perform a position measurement faster with a beam having a small cross-section than with a beam having a larger cross-section. The cross-section of the beam increases in the direction of the target. Therefore, it is preferred to measure the beam position as far as possible in the direction of the source of the beam that the cross-section of the beam corresponds to at the most 80%, preferably 60%, of its cross-section directly before the target.

Preferably, the width of the beam is determined by means of a separate module. In comparison to a solution wherein the width of the beam is determined with the same module with which the position of the beam is determined, it is possible to achieve a velocity advantage. For example, a module can correspond to a complete analysis and/or operation chain from the detector to the software. It can also involve a separate computer or a separate process on the computer, which can already be sufficient to determine the parameters mentioned separately from one another.

The invention also involves a device for irradiating a target with a beam approaching target points, which beam has a measuring device for measuring at least one of the parameters relating to position of the beam and intensity of the beam, and having a sequence control system which is designed to change the beam as a function of the at least one measured parameter, particularly as a function of a variance relating to the at least one measured parameter. The irradiation device is characterized in that it is designed to measure the at least one measured parameter at the most once per target point.

Such an irradiation device comprises also equipment for generating a beam, particularly for generating a particle beam or especially an ion beam. For example, beam generation equipment can involve an accelerator, particularly a synchrotron or cyclotron.

When irradiation is performed by means of an ion beam, the irradiation device comprises also a scanning device, or scanner, which involves scanning magnets for deflecting the ion beam and/or depth modulation device.

Position measurements can be performed by means of an MWPC, a strip ionization chamber, a measuring chamber based on scintillators or PET. The intensity can be measured by means of an ionization chamber (IC) or also with an MWPC, a pixel ionization chamber or also by means of a measuring chamber based on scintillators.

Basically, sequence control systems for generic irradiation devices are known. For example, the above-mentioned publication by Haberer et al. describes one of them. Such sequence control systems typically have the function of controlling irradiation, particularly the scanning process, the maximum dose, making comparisons with a radiation plan and documentation.

If necessary, the sequence control system interferes in the irradiation procedure (interlock), for example by means of an interruption or correction of the irradiation procedure when the beam fluctuates in its intensity, or in the case of other interferences.

For example, the sequence control system can be implemented with the help of a computer or data processing system. It is possible to store in such a computer information regarding the energy distribution of the scans and the iso-energy layers, the target points, the screen dots, the intended dose per screen dot, the treatment plan and criteria for ending the irradiation process. One criterion for ending the irradiation process can involve reaching the intended dose per target point specified in the treatment plan. The criterion of reaching the intended dose can be fed back to the scanning device. It is recommended to document the intended dose per target point in a chart. A respective or at least comparable chart containing all parameters for the sequence control system can also be documented for each scan during the process of rescanning.

The computer can be provided with several modules for each respective function. The data processing system can be provided with several computers for each respective function. Such functions involve, for example: scanner control, pulse control center (requests an ion beam), intensity measurement (at least one, preferably two per target point for increasing redundancy, provided at the most one position measurement has been made), position measurement (at least one, preferably two per target point for increasing redundancy, provided at the most one intensity measurement has been made), documentation. Typically, the beam parameters from the pulse control center, the scanner parameters and the results of the intensity and position measurements are documented.

If the device has several equipments for intensity measuring and position measuring—this can be beneficial for increasing redundancy—it is preferred to connect these in series in order to increase the sampling rate of the measurements and thus reduce the period of measuring. For example, if the device has two equipments, respectively, for intensity measuring and position measuring, and if the respective equipments for intensity measuring and the equipments position measuring connected in series, the respective maximum sampling rate can possibly be doubled. These equipments can involve detectors, modules, computers or evaluation units in general.

Preferably, the irradiation device is designed to perform the invention-based method in any of the preferred embodiments.

The invention also involves a control system for controlling the irradiation device. In contrast to the irradiation device, the control system itself does not comprise a beam generation device. If the control system is used for controlling an irradiation device for irradiating humans or animals, it is also called a therapy control system (TCS).

For example, the invention-based method can be performed by modifying the position measuring device, also called position measuring module (SAM; memory and readout module) which can be part of the control system. For this purpose, the control system receives an additional component or an existing module is replaced. Basically, it is necessary to adjust the control system to the sequence control system, it is possibly sufficient to adjust the control software.

The preceding and the following description of the individual characteristics comprise the method, as well as the device and the control system without mentioning it in every single case. The individual characteristics disclosed here can be of significance also in combinations not shown in this invention.

Subsequently, the invention is explained in more detail also by means of embodiments.

FIG. 3 shows a selection of invention-based measures concerning the measuring of beam position and beam intensity.

Figure 1:
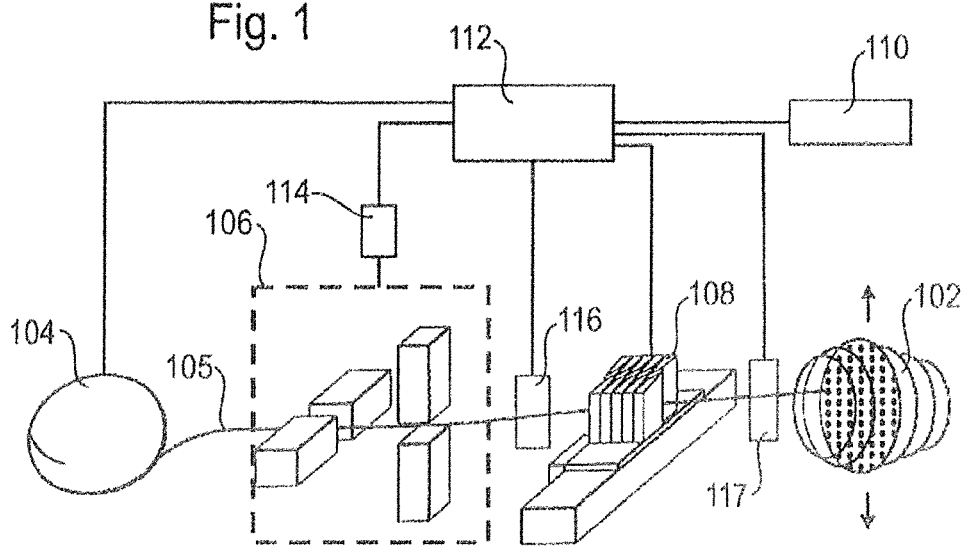
FIG. 1 shows a schematic diagram of an invention-based irradiation device having an invention-based control device for carrying out the invention-based method.

The irradiation device is designed to irradiate a target volume 102. For example, the target volume 102 involves a tumor situated near or in the lung of a person. The target volume 102 shown has a diameter of approximately 20 cm vertically to the beam direction. Alternatively, it can also involve a phantom, for example, based on water or Plexiglas, or any other material. The target volume moves cyclically up and down, which is indicated in FIG. 1 by the arrows above and below the target volume 102.

The irradiation device comprises a synchrotron, a cyclotron or any other accelerator 104 for providing a particle beam 105, consisting, for example, of protons or $^{12}C$ nuclei. Typically, such a beam has an expansion of one or several millimeters, approximately between 3 and 10 mm. In the target volume 102 layers are indicated which correspond to the depth of the Bragg-Peak for a specific particle energy (iso-energy layers).

The scanning method selected here is called grid scanning. The irradiation device uses the particle beam 105 to approach screen dots that are schematically represented in the target volume 102 as black points. These screen dots are located in the target volume approximately 2 mm apart from each other. To simplify matters, a layer-by-layer approach of the screen dots is shown. Alternative, it is also possible to approach the screen dots in volumetric manner (not shown).

The particle beam 105 can be laterally impacted by means of scanning magnets 106. These scanning magnets are dipole magnets 106 in this example. For a longitudinal impact (in beam direction) the irradiation device comprises a passive energy variation system for energy modulation, for example, in the form of a wedge-type system 108. The wedge-type system 108 has wedges, consisting, for example, of plastic material which are moved by means of a linear motor (not shown). Preferably, the wedge-type system 108 is used with volumetric scans. In layer-by-layer scanning, the energy is preferably changed my means of an accelerator or an energy modulation system installed before the scanning magnets 106.

Furthermore, the irradiation device comprises a sequence control system 112, a scanner control 114, a particle counter 116 and a position detector 117. The particle counter 116 and the position detector 117 can also be placed at other positions, for example at the position of the particle counter 116. Here, the sequence control system 112 has the function of a control system.

The particle counter 116 is an ionization chamber (IC) and functions as an intensity measuring device. The position detector 117 is a multi-wire-proportional-chamber (MWPC). The ionization chamber 116 requires 15 μs for an intensity measurement. The multi-wire-proportional-chamber required 150 μs for determining the position of the beam 105. The position of the beam can be measured almost directly before the target or approximately 1 m before the target. Alternatively, it is recommended to measure the position of the beam further in the direction of the beam source because there the beam diameter is smaller and therefore the position measurement can be performed faster. The position detector 117 can be arranged in such a way that the beam diameter amounts to at the most 50% of its value directly before the target.

Two modules, respectively, for determining the intensity and for determining the position of the beam have been provided. Each of them is connected in series (not shown). Here it is possible to obtain a higher temporal resolution, for example, through "time-shift" measurements. To increase safety it is possible to provide redundancy through a comparison that takes the time-shifts into consideration.

The particle counter 116 determines the number of particles in the particle beam 105 and transmits the results to the sequence control system 112. The sequence control system 112 is designed to control the accelerator 104, the scanning magnet 106 and the wedge-type system 108. For this purpose, the sequence control system 112 determines respective control parameters by taking into consideration the data received from the particle counter 116 and the position detector 117.

The irradiation process is performed by means of several scans, using the method of rescanning.

A selection can be made between approximately 5 and 10, preferably 15 to 20, or up to 30 scans. Typically, the target volume is divided in 50 layers. Typically, it takes 100 ms up to 1 s to completely approach a layer. When a volume is approached, the approach period ranges seconds.

Figure 2:
FIG. 2 shows a sequence diagram of the invention-based method.

During the irradiation process, generally at the most one position measurement or at the most one intensity measurement per screen dot is performed, see FIG. 2.

According to the invention, the following measures can be taken for determining the position or intensity of the beam:
- at the most one position measurement per screen dot, no intensity measurement;
- at the most one intensity measurement per screen dot, no position measurement;
- at the most one position measurement per screen dot, as well as one intensity measurement per screen dot;
- at the most one position measurement per screen dot, as well as several intensity measurements per screen dot;

at the most one intensity measurement per screen dot, as well as several position measurements per screen dot;

control of the irradiation procedure according to the intensity of the beam (intensity control). If necessary with several intensity measurements per screen dot, wherein the position of the beam is measured at the most once per screen dot;

at the most one position measurement for three or 10 screen dots or even for one line of screen dots;

at the most one intensity measurement for three or 10 screen dots or even for one line of screen dots;

performance of intensity measurements and/or position measurements according to fixed intervals;

shortest possible selection of intervals;

intensity control of the irradiation process; fixed intervals for the position measurements;

coordination of intervals, so that three or 10 screen dots or even one line of screen dots is approached in between the measurements;

coordination of intervals so that the irradiation time is not increased by the measurements;

averaging a measurement over several screen dots;

taking into consideration the ionization in the detector gas for improving such an averaging process;

timing of irradiation, wherein the positions are measured at the most once per screen dot;

taking into consideration the extraction profile in such timing;

measuring the beam position relatively near the beam source;

the measurement of the width of the beam is performed with a separate module, decoupled from the location measurement;

connecting measuring devices in series;

FIG. 3 shows a selection.

Figures 4, 5:
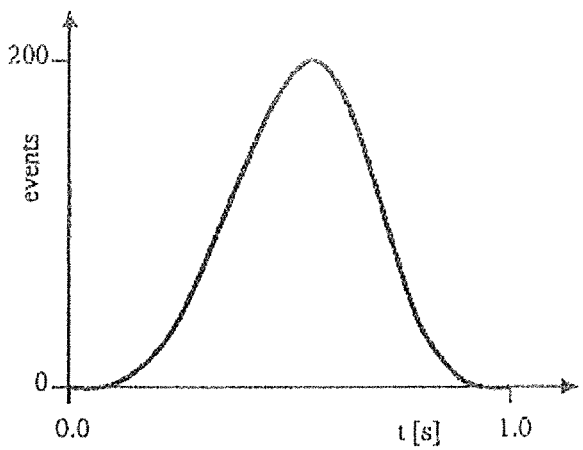
FIG. 4 shows a selection of invention-based measures concerning changes of the beam.
FIG. 5 shows a schematic extraction profile of the device shown in FIG. 1.

According to the invention, the following measures concerning possible changes of the beam resulting from a determination of the position or the intensity of the beam involve:

interrupting the irradiation process if the measured position or the measured intensity considerably deviate from the respective intention;

correcting the beam position if the measured position deviates slightly from its target value;

FIG. 4 shows a selection.

FIG. 5 shows a schematic extraction profile of the device for a krypton beam (shown in FIG. 1) having energy of 300 MeV/u. In addition to rise and fall, a real (synchrotron) profile would comprise also a plateau with fluctuations, a so-called "ripple". It can be observed that the particle number (events) per extraction (spill) initially increases rapidly. after approximately half a second, it reaches a maximum, and after one second it basically dropped again to zero. When the approach of the screen dots is not controlled by means of the intensity of the beam, but in temporal manner, said extraction profile for determining the scan speed is taken into consideration. If the number of extracted particles is especially high, it is possible to select a fast scan speed; if it s low a slow scan speed is selected.

The invention claimed is:

1. Method for irradiating a target (102) with a beam (105) approaching target points, involving the following steps:

Measuring at least one of the parameters relating to the position of the beam and the intensity of the beam, changing the beam as a function of the at least one measured parameter, particularly as a function of a variance relating to the at least one measured parameter, characterized in that the at least one measured parameter is measured at the most once per target point;

wherein the approach of the successive target points is determined by the elapsed time or by the extraction profile.

2. Method according to claim 1, wherein the position of the beam (105) is measured at the most once per target point.

3. Method according to claim 1 or 2, wherein the irradiation process is designed a multiple irradiation with at least two scans, wherein in each of the scans target points are approached successively.

4. Method according to claim 3, wherein the target (102) is moved.

5. Method according to any one of the preceding claims, wherein the at least one measured parameter is measured at the most once for at least two target points.

6. Method according to any one of the preceding claims, wherein the points in time of the measurement of the at least one measured parameter is determined by the elapsed time.

7. Method according to any one of the preceding claims, wherein the beam position is measured as far in the direction of the source of the beam (104) that the cross-section of the beam (105) corresponds to at the most 80% of the cross-section of the beam directly before the target.

8. Method according to any one of the preceding claims, wherein the width of the beam (105) is measured with a beam width measuring module.

9. Device for irradiating a target (102) with a beam (105) approaching target points comprising a measuring device (116, 117) for measuring at least one of the parameters relating to the position (117) of the beam (105) and the intensity (116) of the beam (105), and comprising a sequence control system (112) designed to change the beam (105) as a function of the at least one measured parameter, particularly as a function of a variance relating to the at least one measured parameter, characterized in that the device is designed to measure the at least one measured parameter at the most once per target point;

wherein the approach of the successive target points is determined by the elapsed time or by the extraction profile.

10. Device according to claim 9, wherein several measuring devices are connected in series.

11. Device according to claim 9 or 10, designed to perform a method in accordance with claims 1 to 10.

12. Control system (112) for controlling a device in accordance with any one of claims 9 to 11.

* * * * *